US009333105B2

(12) United States Patent
Lane

(10) Patent No.: US 9,333,105 B2
(45) Date of Patent: May 10, 2016

(54) WRIST SUPPORT DEVICE

(71) Applicant: Christi Lane, Austin, TX (US)

(72) Inventor: Christi Lane, Austin, TX (US)

(73) Assignee: Christi Lane, Austin, TX (US)

( * ) Notice: Subject to any disclaimer, the term of this patent is extended or adjusted under 35 U.S.C. 154(b) by 83 days.

(21) Appl. No.: 14/159,688

(22) Filed: Jan. 21, 2014

(65) Prior Publication Data

US 2014/0207039 A1 Jul. 24, 2014

Related U.S. Application Data

(60) Provisional application No. 61/755,279, filed on Jan. 22, 2013.

(51) Int. Cl.
*A61F 5/00* (2006.01)
*A61F 5/01* (2006.01)

(52) U.S. Cl.
CPC ....... *A61F 5/0118* (2013.01); *A61F 2005/0181* (2013.01)

(58) Field of Classification Search
CPC .. A61B 5/0205; A61B 5/14532; A61B 5/681; A61B 7/04; A61B 17/32002; A61B 19/201; A61B 2017/00084; A61B 2017/0023; A61B 2017/3409; A61B 2560/0412; A61B 3/0008; A61B 3/1208; A61B 3/125; A63B 24/0062; A63B 2071/0655; A63B 21/0004; A63B 21/00196; A63B 21/0058; A63B 21/023; A63B 21/0442; A63B 21/0552; A63B 21/0557; A63B 21/1415; A63B 21/143; A63B 21/1438; A63B 21/1449; A63B 23/16; A63B 21/00061; A63B 21/0555; A63B 23/14; A63B 2021/222; A63B 21/00069; A63B 21/028; A61M 5/20; A61M 2005/206; A61M 2205/50; A61M 2205/502; A61M 2205/505; A61M 2205/583; A61M 2205/586; A61M 2205/8206; A61M 5/3134; A61M 5/3202; A61M 5/3204; A61M 5/326; A61M 16/0816
USPC .................................. 602/21–23; 482/44–50
See application file for complete search history.

(56) References Cited

U.S. PATENT DOCUMENTS

| 5,013,030 | A | * | 5/1991 | Frins | 482/47 |
| 5,326,340 | A | * | 7/1994 | Coffey | 482/93 |
| 6,511,403 | B2 | * | 1/2003 | Hsieh | 482/45 |
| 8,591,384 | B2 | * | 11/2013 | Marji | 482/50 |
| 2007/0167301 | A1 | | 7/2007 | Evans | |
| 2011/0053739 | A1 | | 3/2011 | Andrews | |
| 2012/0065027 | A1 | * | 3/2012 | Zachary | 482/48 |

* cited by examiner

*Primary Examiner* — Michael Brown
(74) *Attorney, Agent, or Firm* — William N. Hulsey; Jeffrey D. Hunt; Hulsey Hunt & Parks, P.C.

(57) ABSTRACT

A support device for protecting one or more portions of a user's hand or arm by limiting movement thereof includes a base surface for contacting a floor or other object adjacent to the device, a curved support surface extending from the base surface, and a plurality or orifices formed in the support surface. A user's fingers and thumb can be placed through the orifices to allow the palm of the hand to rest on a portion of the support surface, suspending the heel of the hand above the support device and aligning the user's wrist with the heel. The fingers may remain freely suspended within the device.

16 Claims, 10 Drawing Sheets

WRIST SUPPORT DEVICE

CROSS-REFERENCE TO RELATED APPLICATIONS

The present application claims priority to the United States provisional application for patent having the Application Ser. No. 61/755,279, filed Jan. 22, 2013, which is incorporated by reference herein in its entirety.

FIELD OF THE INVENTION

Embodiments usable within the scope of the present disclosure relate, generally, to support devices usable in conjunction with a human body, and more specifically, to support devices usable, e.g., during exercise or physical activity involving a user's hand, fingers, wrist, and/or forearm.

BACKGROUND OF THE INVENTION

Injuries to an individual's fingers, hand, wrist, and forearm are common occurrences during exercise, sporting events, and/or other types of recreational and/or professional physical activity. Injuries can be the result of a single trauma to the afflicted area (e.g., an impact or irregular movement during an exercise or sporting event) or can result from repetitive motions (e.g., overuse/overtraining associated with exercise).

While various types of devices for providing support to the fingers, wrist, and forearm exist, such devices typically allow extension of the wrist to occur, which can cause pain and injury. For example, wedge-shaped devices designed to support a user's hand allow much of the user's weight to be placed in the heel of the hand, rather than positioning the hand in a neutral position, which can lead to strain and wrist extension. Long cylindrical devices used to promote alignment of a user's hand and/or forearm typically require the user to shift his or her weight must be in a forward direction, toward the fingers, to straighten the wrist into a proper neutral position. Some support devices require a user to grip at least a portion of the device with his or her fingers, such that a significant amount of strength is required to use the device, which can lead to muscular strain.

Other types of support devices include a rounded bottom to create instability, requiring the user to utilize muscles in the wrist to maintain balance, eventually strengthening these muscles. Some devices of this type incorporate a flexible compressible body. While use of such devices may eventually strengthen the muscles in the wrist, use of these devices may damage or injure these muscles and/or aggravate preexisting injuries of a user.

A need exists for support devices usable during exercise, sporting events, athletic activities, and/or other types of physical activity, that protect the hand, wrist, fingers, thumb, and/or forearm from injury, e.g., by limiting movement thereof.

BRIEF SUMMARY OF THE INVENTION

Embodiments usable within the scope of the present disclosure relate to support devices and methods usable to protect a user's hand (e.g., the palm, heel, fingers, thumb, wrist, metacarpophalangeal joints, and/or forearm associated therewith) by limiting movement thereof, e.g., during exercise or other physical activities. For example, during such activities, it may be desirable to prevent unwanted extension, flexion, radial deviation, pronation, supination, and/or other potentially damaging movements that can occur during various types of exercise not involving tension in the muscles and tendons related to these movements. Ensuring proper alignment of an individual's fingers, wrist, and forearm can reduce the potential for such movements and/or associated injuries, and embodiments usable within the scope of the present disclosure can facilitate such alignment, e.g., by directing a load applied by a user's hands in a forward direction.

In an embodiment, a support device can include a base surface (e.g., a generally flat surface) adapted to contact an adjacent object (e.g., the ground, a floor, a mat, and/or similar supporting surface) and a support surface (e.g., having a curved and/or arcuate shape) extending from the base surface. A plurality of orifices can be formed in the support surface.

In use, the digits (e.g., the fingers and thumb) of a user's hand can be passed through the orifices. In an embodiment, one or more orifices for accommodating the fingers can be positioned toward a front side of the support surface while an orifice for accommodating the thumb can be posterior to the orifices for receiving the fingers. Placement of the fingers and thumb in the orifices allows a portion of the hand (e.g., the center of the palm and/or the metacarpophalangeal joints), to contact at least a portion of the support surface (e.g., the portion extending between the orifice accommodating the thumb and the one or more orifices accommodating the fingers). Proper alignment of the fingers, wrist, forearm and/or other portions of the hand can be facilitated by supporting the hand in this manner. In an embodiment, contact between the fingers and/or thumb and the base and support surfaces can be minimized. For example, the fingers can be suspended through the orifices without contacting any structure, padding, or other material; essentially, contact between the support surface and the hand can allow the fingers and thumb to remain suspended in the absence of any structure intended to contact the fingers/thumb.

In an embodiment, the base surface can be angled (e.g., positioned at a 15 degree angle relative to a horizontal surface, or another suitable angle) to direct the load applied to the support device by a hand toward the front side of the device, thereby reducing the force applied to the heel of the hand while facilitating the application of the force on the palm of the hand. Directing the load in this manner can also cause at least a small amount of force to be applied to the metacarpophalangeal joints. In an embodiment, one or more portions of the support surface can include padding intended to contact the metacarpophalangeal joints.

In a similar manner, the support surface can have an angled dome shape and/or the orifices formed therein can have an angled orientation, adapted to direct the load of the hand toward the front side of the device to facilitate application of the force to the central palm of the hand, rather than the heel. In an embodiment, the heel of the hand can thereby be substantially suspended, e.g., such that little to no weight is applied thereto.

While embodied support devices can be fabricated from any manner of material able to withstand the forces applied thereto, in an embodiment, the support device can be formed at least partially from a rigid material to facilitate supporting a user.

In use, the support device can enable a user's fingers, wrist, and forearm to remain in a neutral position during physical activity. By maintaining the hand in an open, anatomically neutral position, the ligaments of the hands remain in a neutral position, while compression of the bursa, ligaments, and nerves, often caused by extension of the wrist under load, can be prevented.

In an embodiment, the support device can lack wraps, straps, or other types of structure across the back of the hand, for facilitating quick insertion and removal of a user's hand. Portions of the device can vary in size to accommodate different sizes and shapes of hands.

BRIEF DESCRIPTIONS OF THE FIGURES

Embodiments usable within the scope of the present disclosure can be understood by reference to the following detailed description of illustrative embodiments, read in conjunction with the accompanying figures.

DETAILED DESCRIPTION

Embodiments usable within the scope of the present disclosure include support devices and methods usable to support and/or position a user's hand (e.g., the fingers, wrist, and/or forearm thereof), for preventing injury thereto. For example, embodiments described herein can retain a user's fingers, wrist, and forearm in a neutral position during weight-bearing activity in which the user's hands may contact a surface or equipment and/or tools (e.g., weights and/or weighted machines). Specifically, embodiments usable within the scope of the present disclosure can reduce or prevent undesired extension, flexion, radial deviation, pronation, and/or supination motions during exercise, and reduce or eliminate tension in muscles and/or tendons in the hand, fingers, forearm, and/or wrist related to exercise or other physical activity. Maintaining the hand in an anatomically neutral position can ensure that the ligaments thereof are in a neutral position, preventing compression of the bursa, ligaments, and nerves due that can be caused by extension of the wrist.

In various embodiments, support devices can be used without requiring any specific level of strength in a user's hand, fingers, wrist, and/or forearm, nor is anatomical knowledge necessary for use of the device. For example, upon insertion of the hand into an embodied device, it is not necessary for the fingers to enclose or grasp an object; instead, the fingers can be suspended freely, e.g., in a hollow body of the device, such that the fingers remain free from any weight or pressure. In an alternate embodiment, the fingers can rest on an external surface of the device without a surrounding enclosure.

Similarly, in various embodiments, the support device can be used without requiring a wrap, strap, or similar securing device to be placed around the hand; simple insertion of a user's hand can be sufficient to engage and utilize the device, while portions of the device can be varied in size to facilitate a proper fit. In other embodiments, the device may be adjustable such that a single device can accommodate different sizes. The absence of wrappings or straps to secure the hand can quick and easy insertion and removal from the device.

In some embodiments, the position of the hand can allow the heel of the hand to remain lifted and/or suspended, bearing little or no weight. Instead, the majority of a user's weight can be placed near the center of the palm, which can contact a support surface of the device, while a small amount of weight could be distributed across the metacarpophalangeal joints (knuckles). In an embodiment, padding can be placed on the device in areas where the metacarpophalangeal joints (knuckles) rest.

Figure 1:
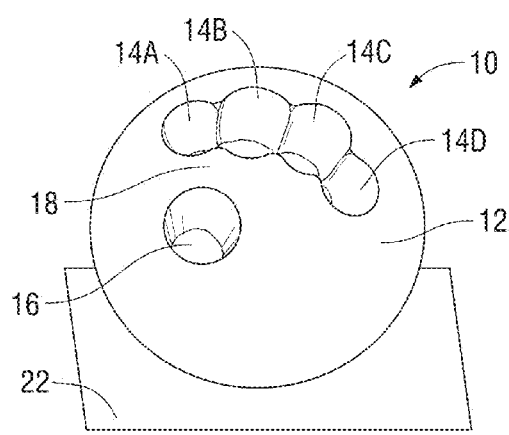
FIG. 1 depicts a top view of an embodiment of a support device usable within the scope of the present disclosure.

FIG. 1 depicts a top view of an embodiment of a support device (10) usable within the scope of the present disclosure. The device is depicted having a generally flat, angled base surface (20, visible in FIGS. 2A, 2B, and 2C), from which a support surface (12), having a curved and/or domed shape, extends. Four adjacent orifices (14A, 14B, 14C, 14D) adapted for receiving a user's fingers are formed in the support surface (12). While FIG. 1 depicts the orifices (14A, 14B, 14C, 14D) as connected and/or contiguous orifices, it should be understood that in various embodiments, one or multiple contiguous or separated orifices could be used without departing from the scope of the present disclosure. Alternatively or additionally, one or more orifices can be formed on the exterior of the support surface (12), e.g., having the form of grooves, notches, indentations, etc., as described below with reference to other embodiments. An additional orifice (16) is shown positioned in the support surface (12), posterior relative to the other orifices (14A, 14B, 14C, 14D). In use the additional orifice (16) can accommodate a user's thumb, such that the center of the user's palm rests on a weight-bearing region (18) of the support surface (12), located between the first set of orifices (14A, 14B, 14C, 14D) and the additional orifice (16). Positioning of the additional orifice (16) for accommodating the thumb posterior relative to the other orifices (14A, 14B, 14C, 14D) allows greater contact between the hand and the weight-bearing region (18), increasing the surface area thereof. In an embodiment, at least a portion the body of the support device (10) can be generally hollow, such that the fingers and/or thumb are simply suspended within the device after insertion through the orifices.

Figure 2A:
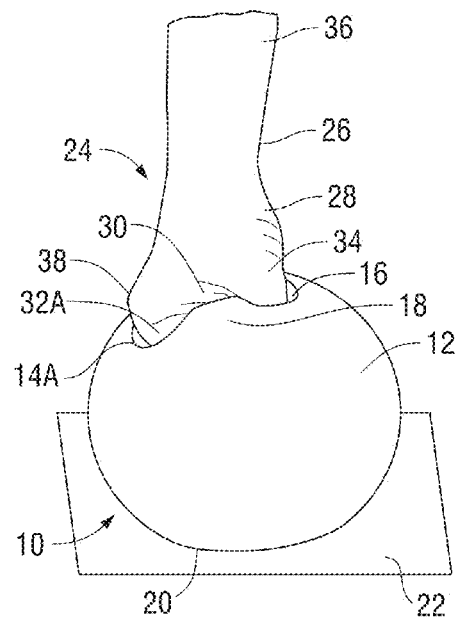
FIG. 2A depicts a side view of the device of FIG. 1, having a user's hand engaged therewith.
Figure 2B:
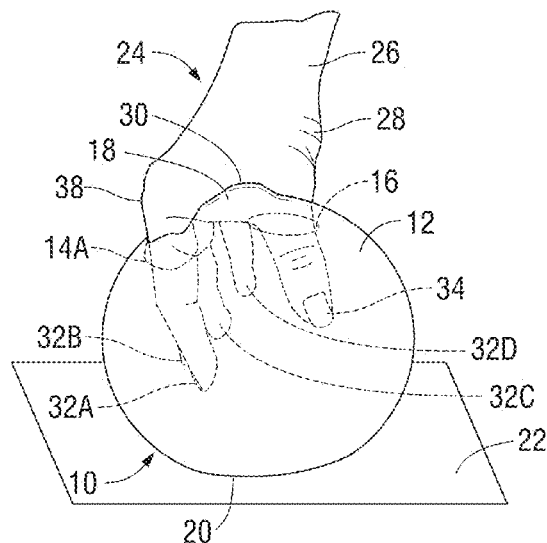
FIG. 2B depicts the device of FIG. 2A with the position of the fingers of the user's hand shown.

FIG. 2A depicts a side view of the support device (10), having a hand (24) associated therewith. FIG. 2B depicts a diagrammatic side view of the support device (10) and hand (24), having the position of each of the digits of the hand (24) within the device (10) illustrated. As described above, the support device (10) is shown including a flat, angled base surface (20) positioned against a floor (22) or similar adjacent object (a mat, a piece of exercise equipment, etc.), a curved/arcuate support surface (12), orifices for accommodating fingers of which a first orifice (14A) is visible, and an additional orifice (16). The hand (24) is shown having a wrist (26), heel (28), palm (30), four fingers (32A, 32B, 32C, 32D), thumb (34), forearm (36), and metacarpophalangeal joints (knuckles) (38) associated therewith.

In use, each of the fingers (32A, 32B, 32C, 32D) is inserted into a respective orifice (14A, 14B, 14C, 14D), and the thumb (34) is inserted in the additional orifice (16), such that the palm (30) contacts the weight-bearing portion (18) of the support surface (12). As illustrated in FIG. 2B, the interior of the support device (10) can lack any internal structure that contacts the fingers (32A, 32B, 32C, 32D) or thumb (34), such that the digits simply remain suspended within the body of the device (10), e.g., in a neutral position, without gripping any structure and/or bearing any significant amount of weight (e.g., such that it is not necessary for any muscular force to be applied by the hand).

The majority of the load applied by the hand (24) is supported by the palm (30) thereof, through contact with the weight-bearing portion (18) of the support surface (12). In an embodiment, a portion of the weight can also be borne by the metacarpophalangeal joints (38), which can contact a portion of the support surface (12) anterior of the orifices (14A, 14B, 14C, 14D).

Figure 2C:
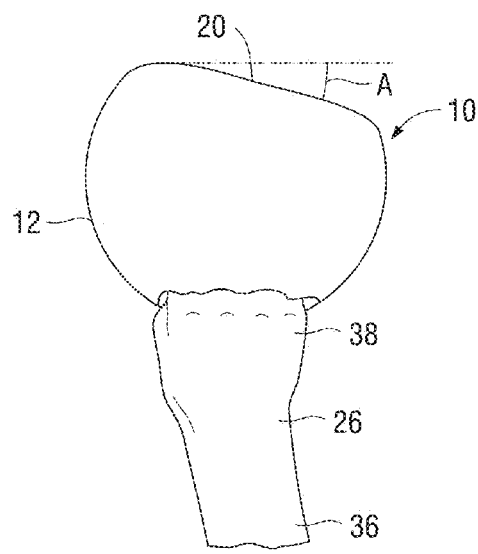
FIG. 2C depicts a rotated side view of the device of FIG. 2A.

In an embodiment, the base surface (20) of the device (10) can be angled, as illustrated, for example, in FIG. 2C, which depicts a rotated side view of the device (10), showing the angle (A) of the base surface (20) relative to a horizontal surface (e.g., the floor (22) or a similar surface). The angle (A) of the base surface (20) can serve to direct the load applied by the hand (24) toward the front portion of the device (10), such that the majority of the user's weight is borne by the palm (30) and metacarpophalangeal joints (38) via contact with the weight-bearing portion (18) and the portion of the support surface (12) anterior of the orifices (14A, 14B, 14C, 14D). While the angle (A) can vary depending on the intended use of the device (10), the surface against which the device (10) is placed, and/or physical characteristics of the user's body, in an embodiment the angle (A) can be approximately 15 degrees. As shown, for example, in FIG. 2B, the orifices (14A, 14B, 14C, 14D, 16) within which the fingers (32A, 32B, 32C, 32D) and thumb (34) are retained can be angled to facilitate proper positioning of the hand (24). Similarly, the shape, angle, and/or curvature of the support surface (12), including the weight-bearing portion (18) thereof, can be selected to position the hand (24) as illustrated in FIGS. 2A, 2B, and 2C. For example, FIGS. 2A and 2B depict the support surface (12) having an angled dome shape, including a protruding portion along the weight-bearing portion (18) that contact the palm (30).

The angle of the base surface, orifices, and/or support surface can be adapted to direct the weight of the user toward the front side of the device, which can prevent wrist extension. The angle of the base relative to the position at which the hand is inserted or rest can be oriented to position a user's center of gravity away from the heel of the hand, which prevents the heel from bearing weight or achieving an undesired position of extension, which occurs commonly during most activities when weight is placed on the hand.

In use, the support device (10) can facilitate positioning of the fingers (32A, 32B, 32C, 32D), wrist (28), and forearm (26) in a neutral alignment that prevents undesired extension and/or other movements, tension on the ligaments, bursa, etc. Additionally, positioning of the hand (24) in the manner illustrated in FIGS. 2A and 2B can substantially suspend the heel (28) of the hand (24) above the device (10), such that no weight is borne thereon, while the majority of the load applied by the hand (24) is supported by the palm (30), and in an embodiment, partially by the metacarpophalangeal joints (38).

Figure 3:
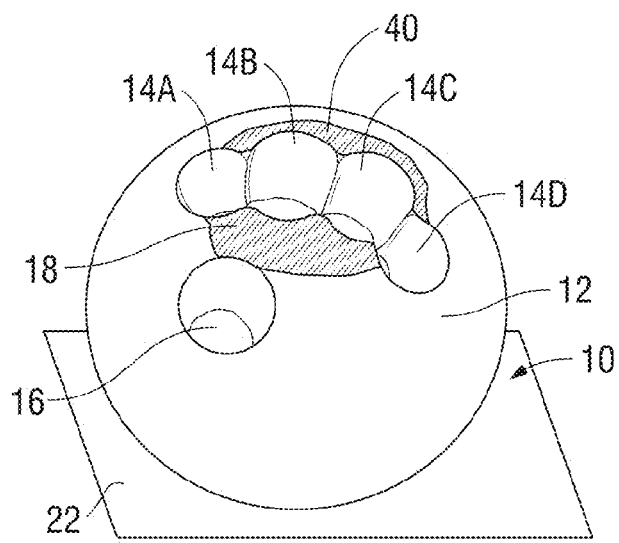
FIG. 3 depicts a diagrammatic top view of the device of FIG. 1, illustrating weight-bearing areas of the device.

FIG. 3 depicts a diagrammatic top view of the support device (10), in which the support surface (12) and orifices (14A, 14B, 14C, 14D, 16) are visible, highlighting the regions of the support surface (12) that will typically bear weight when a hand is associated with the device (10). For example, the weight-bearing region (18) is shown, which would typically bear the majority of a load through contact with a user's palm, while a front support region (40) can bear weight applied by a user's metacarpophalangeal joints. In an embodiment, the front support region (40) and/or the orifices (14A, 14B, 14C, 14D) can include padding and/or other types of compressible material that contacts the metacarpophalangeal joints.

As such, the depicted embodiment lacks any internal structures that interact with the fingers and/or thumb of a user's hand upon insertion into the orifices; the device is a generally solid, unitary structure within and upon which the hand rests in a neutral position once engaged therewith, without requiring gripping and/or muscular effort to be exerted by the hand. Similarly, the depicted embodiment lacks padding or other structure and/or materials within the orifices. No structure, cushioning and/or other materials are used to contact or support the wrist area, allowing the wrist to remain free of pressure and elevated in free space above the device, aligned with the heel, which is also suspended, bearing no weight.

Embodiments usable within the scope of the present disclosure can be used in conjunction with a second support device (e.g., a similar or identical, mirror-image device intended for use with the user's other hand), enabling both hands of a user to be engaged and supported, e.g., during exercises or activities requiring that both hands be protected.

While the support device (10) is shown having a generally flat base and a generally spherical support surface, the device can have any shape and orientation for facilitating the ability of the hand and wrist to rest in a straight, anatomically neutral position. In some embodiments the device may be generally spherical. In other embodiments the device may be, for example, generally cubical, rectangular, triangular, etc. In other embodiments, the base may be of other shapes to allow it to rest on a surface (e.g., an irregular surface) for physical activity. In an embodiment, the device may be rigid and inflexible to maximize the support provided to a user's body. Exemplary usable materials can include foams, urethanes, polymers, plastic, metal, wood, rubbers, clays, and/or plasters.

Figure 4:
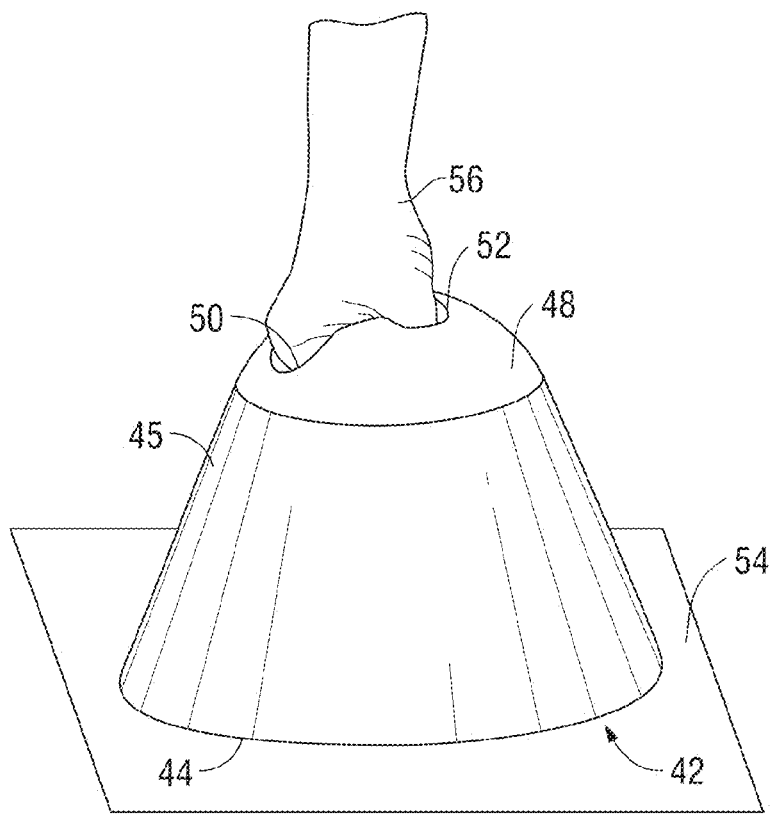
FIG. 4 depicts a side view of an embodiment of a support device usable within the scope of the present disclosure.

It should be understood that while FIGS. 1 through 3 depict an embodiment of a support device generally usable to support a user in a generally perpendicular orientation relative to a floor or other flat surface, and relatively close to the floor or surface, in various embodiments, a usable support device can be sized and shaped, as needed, to position a user relative to any surface or device, at any desired distance therefrom. For example, FIG. 4, depicts an embodiment of a support device (42) having a user's hand (56) engaged therewith. The depicted device (42) includes a base surface (44) that is generally flat and angled relative to a support surface (48) extending therefrom such that the hand (56) can remain in a generally neutral, aligned position when the device (42) is associated with an angled surface (54). A generally conical body (45) is shown extending from the base surface (44), terminating in the support surface (48), which in turn includes orifices (50, 52) for receiving digits associated with the hand (56), as described above. The conical body (45) provides the device (42) with a desired height, such that the hand (56) can be spaced a distance from the angled surface (54). Additionally, the conical body (45) provides the device (42) with a wide base to facilitate stability thereof.

It should be understood that the embodiments depicted in FIGS. 1 through 4 are merely illustrative examples, and that support devices having any desired shape, height, and/or angled surfaces could be formed to allow for proper positioning of a hand relative to any type of surface or device. For example, in an embodiment the base and/or body of a device could be adapted to attach and/or mount to a pole, rod, or similar elongate member, a piece of exercise equipment, or other similar structures and/or devices.

Figure 5A:
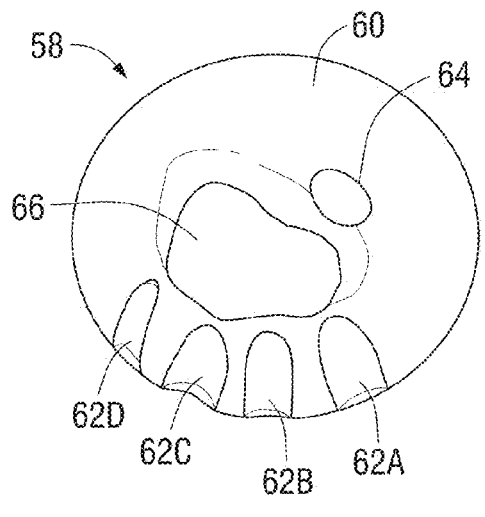
FIG. 5A depicts a top view of an embodiment of a support device usable within the scope of the present disclosure.
Figure 5B:
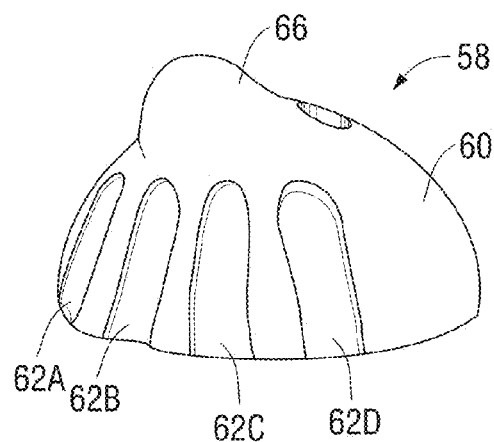
FIG. 5B depicts a side view of the device of FIG. 5A.

FIGS. 5A and 5B, respectively, depict top and side views of an alternate embodiment of a support device (58) usable within the scope of the present disclosure. The depicted device (58) includes a generally flat base surface (61, labeled in FIGS. 6A and 6B)) having a curved and/or arcuate support surface (60) extending therefrom. Formed in the support surface (60), along a front edge thereof, are a plurality of orifices (62A, 62B, 62C, 62D) for engaging a user's fingers, the orifices (62A, 62B, 62C, 62D) taking the form of grooves, recessions, and/or indentations adapted to receive and partially enclose the fingers without requiring full enclosure thereof. An additional orifice (64) for receiving a user's thumb is positioned posterior relative to the first set of orifices (62A, 62B, 62C, 62D). A weight-bearing portion (66) of the support surface (60) is positioned between the additional orifice (64) and the first set of orifices (62A, 62B, 62C, 62D) for contacting the palm of a user's hand. In the depicted embodiment, the weight-bearing portion (66) is shown having an angled dome shape extending outward from the support surface (60) and toward the first set of orifices (62A, 62B, 62C, 62D).

Figure 6A:
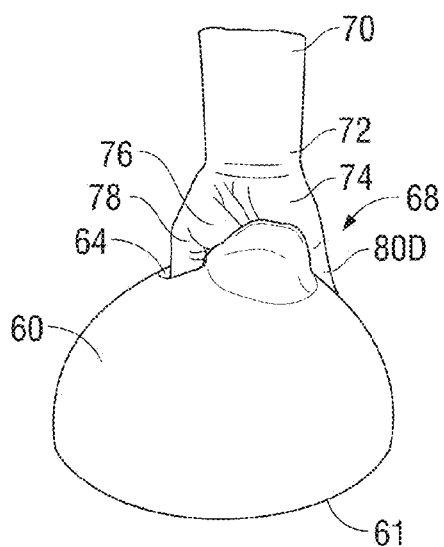
FIG. 6A depicts a back view of the support device of FIG. 5A, having a user's hand engaged therewith.
Figure 6B:
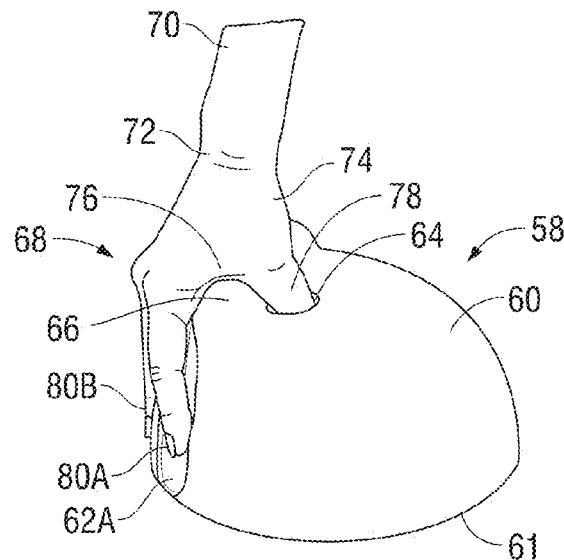
FIG. 6B depicts a side view of the support device of FIG. 6A.

FIG. 6A depicts a rear view of the support device (58) shown in FIGS. 5A and 5B, having a hand (68) associated therewith. FIG. 6B depicts a side view of the hand (68) and support device (58). The hand (68) is shown having a forearm (70), wrist (72), heel (74), palm (76), four fingers of which two fingers (80A, 80B, 80D) are visible in FIGS. 6A and 6B, and a thumb (78). Each finger (80A, 80B, 80D) is placed within a respective orifice (62A, 62B, 62C, 62D), while the thumb (78) is placed within the additional orifice (64), such that the palm (76) contacts the weight-bearing portion (66) of the support surface (60).

Insertion of the fingers (80A, 80B, 80D) and thumb (78) into respective orifices (62A, 62B, 62C, 62D, 64) while contacting the weight-bearing portion (66) with the palm (76) can enable the hand (68) to achieve a generally neutral position in which the forearm (70), wrist (72), heel (74), and fingers (80A, 80B, 80D) are aligned, while the heel (74) is suspended above the device (58) such that no significant weight is placed thereon. Positioning the hand (68) as depicted in FIGS. 6A and 6B can avoid extension, supination, and other undesired motions and/or stresses on the ligaments and other portions thereof.

Figure 7A:
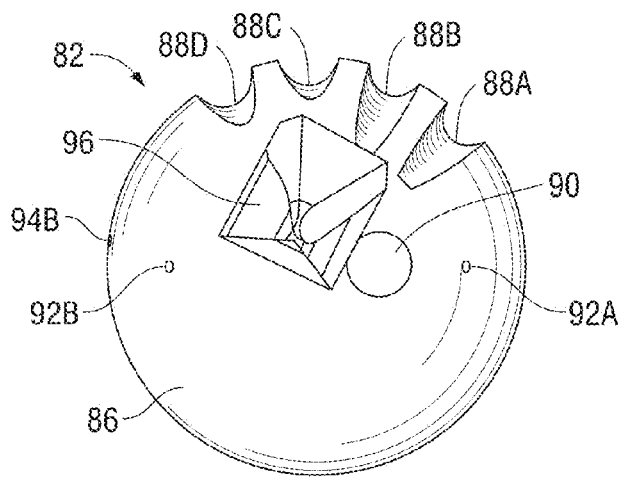
FIG. 7A depicts a top view of an embodiment of a support device usable within the scope of the present disclosure.
Figure 7B:
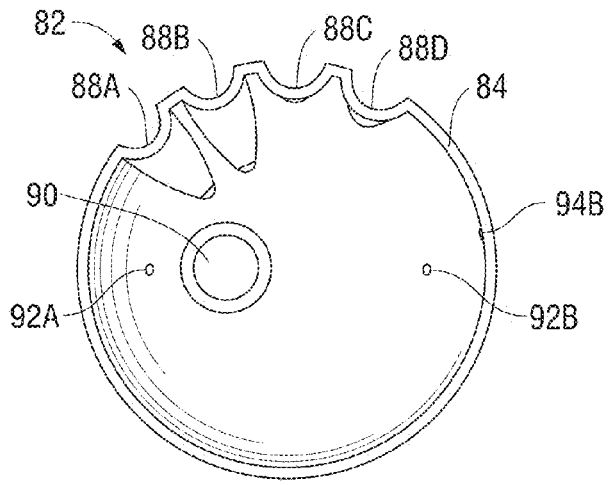
FIG. 7B depicts a bottom view of the support device of FIG. 7A.
Figure 7C:
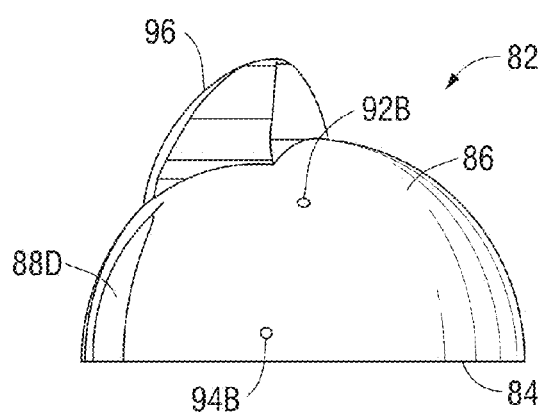
FIG. 7C depicts a left side view of the support device of FIG. 7A.
Figure 7D:
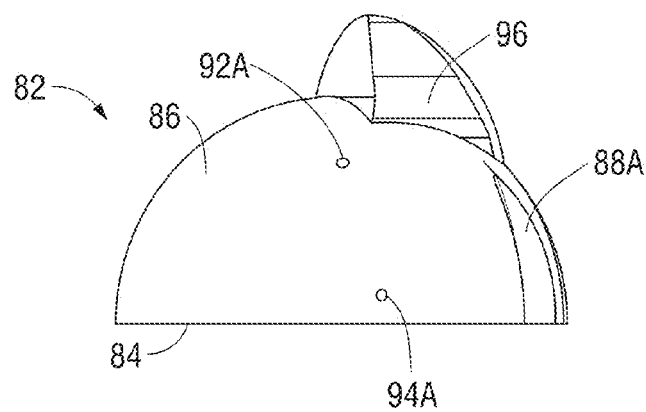
FIG. 7D depicts a right side view of the support device of FIG. 7A.
Figure 7E:
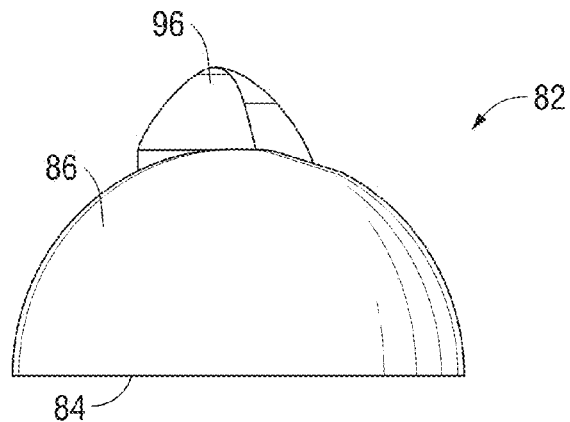
FIG. 7E depicts a back view of the support device of FIG. 7A.
Figure 7F:
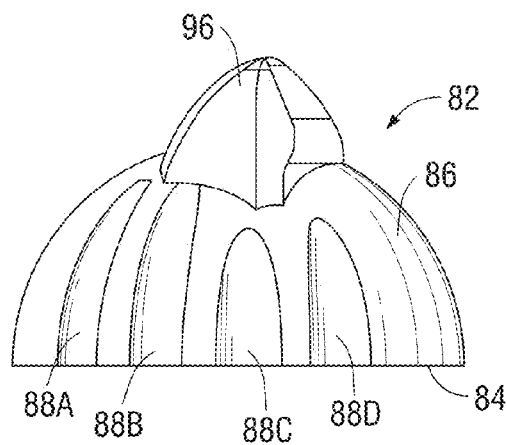
FIG. 7F depicts a front view of the support device of FIG. 7A.
Figure 8A:
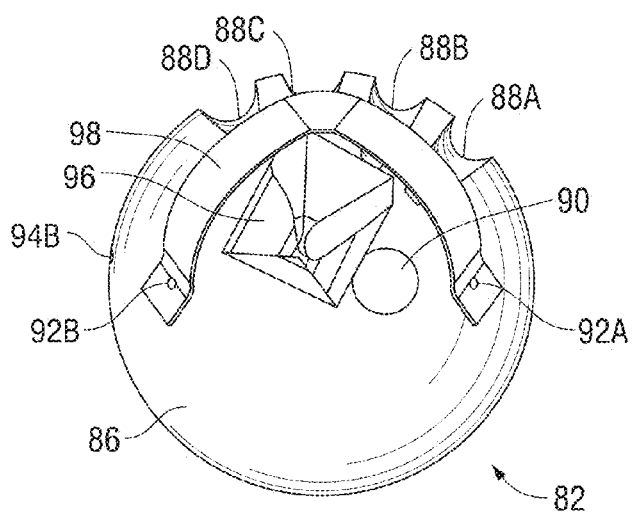
FIG. 8A depicts a top view of the support device of FIG. 7A, having a strap engaged therewith.
Figure 8B:
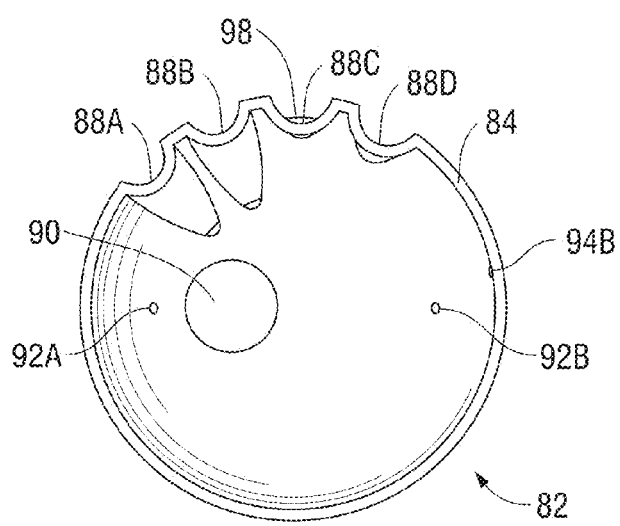
FIG. 8B depicts a bottom view of the support device of FIG. 8A.
Figure 8C:
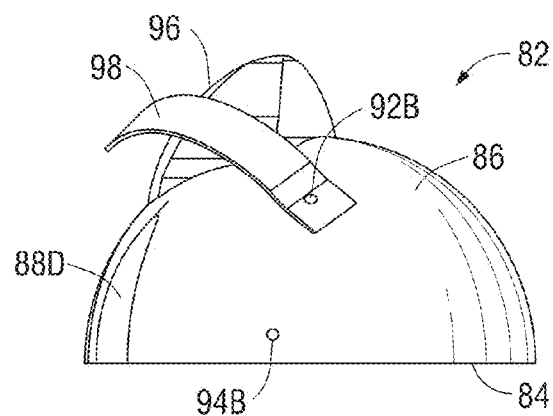
FIG. 8C depicts a left side view of the support device of FIG. 8A.
Figure 8D:
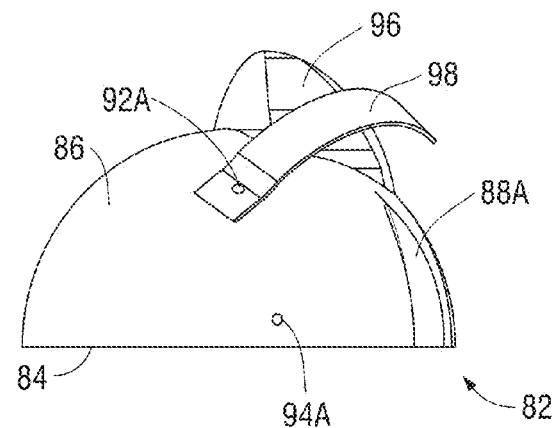
FIG. 8D depicts a right side view of the support device of FIG. 8A.
Figure 8E:
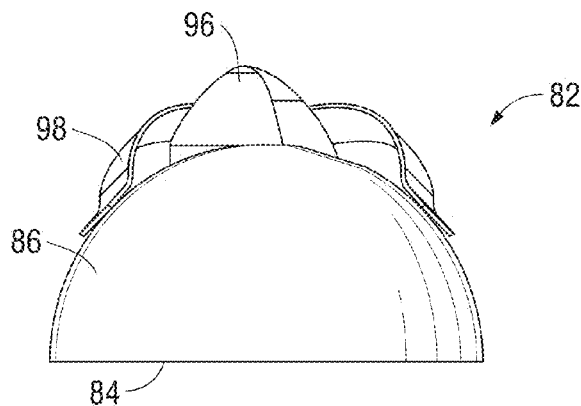
FIG. 8E depicts a back view of the support device of FIG. 8A.
Figure 8F:
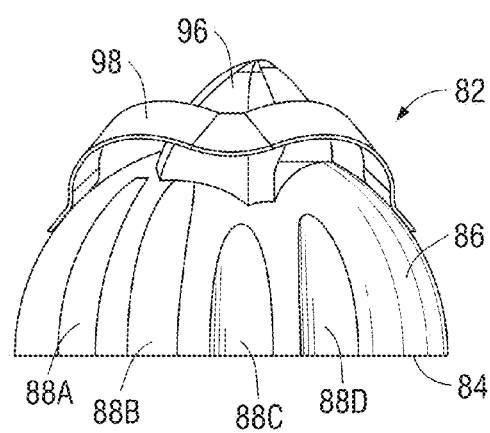
FIG. 8F depicts a front view of the support device of FIG. 8A.
Figure 9A:
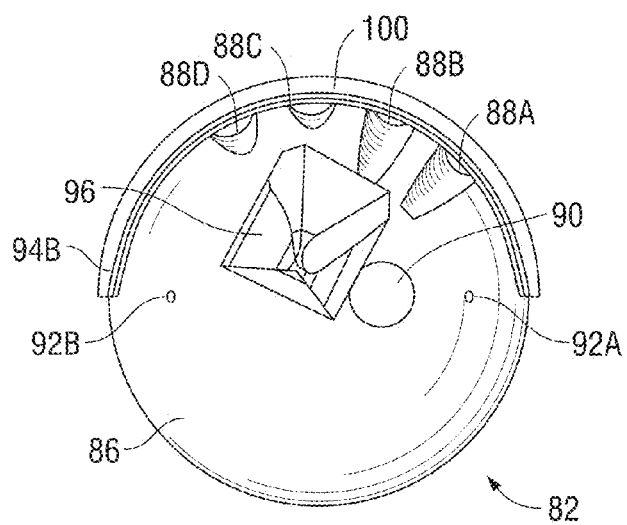
FIG. 9A depicts a top view of the support device of FIG. 7A, having a band engaged therewith.
Figure 9B:
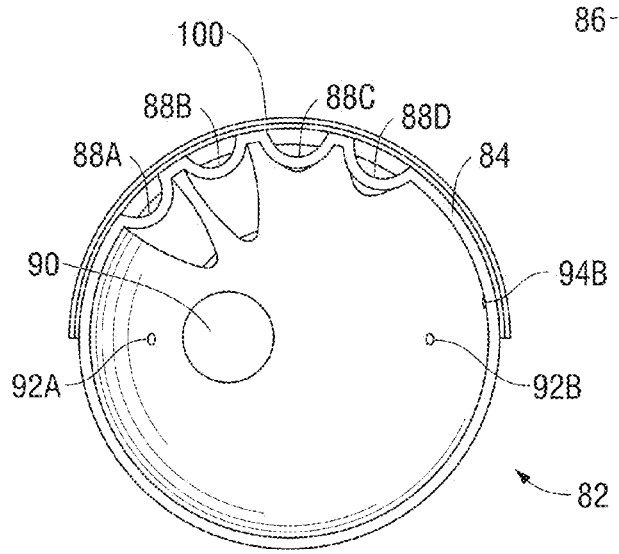
FIG. 9B depicts a bottom view of the support device of FIG. 9A.
Figure 9C:
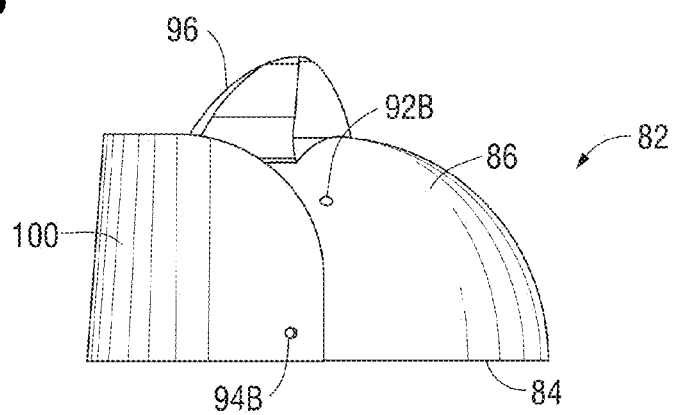
FIG. 9C depicts a left side view of the support device of FIG. 9A.
Figure 9D:
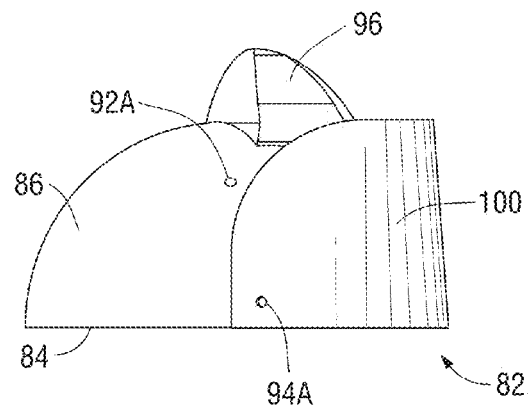
FIG. 9D depicts a right side view of the support device of FIG. 9A.
Figure 9E:
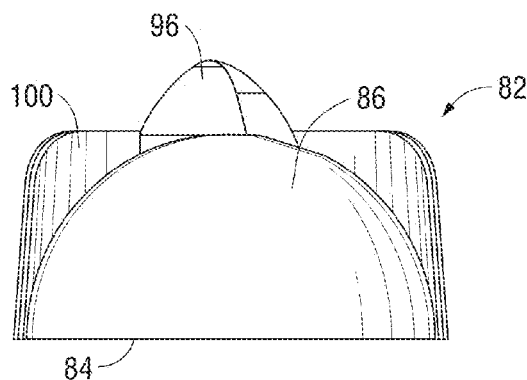
FIG. 9E depicts a back view of the support device of FIG. 9A.
Figure 9F:
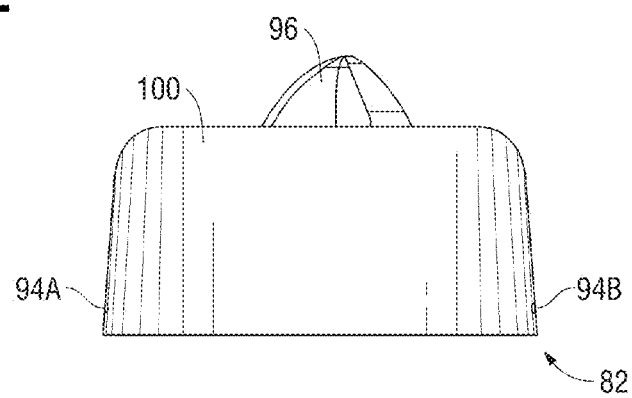
FIG. 9F depicts a front view of the support device of FIG. 9A.

FIGS. 7A through 7F depict an embodiment of a support device (82) usable within the scope of the present disclosure in which FIG. 7A depicts a top view of the support device (82), FIG. 7B depicts a bottom view, FIG. 7C depicts a left side view, FIG. 7D depicts a right side view, FIG. 7E depicts a back view, and FIG. 7F depicts a front view thereof. The depicted support device (82) is shown having a generally dome and/or hemispherical shape, with a hollow/concave interior, and in an embodiment, can be formed from a generally rigid material (e.g., plastic, metal, wood, rubber, polymers, etc.) for supporting the weight of a user.

The depicted support device (82) includes a generally flat base surface (84), shown, e.g., as the rim of the dome/hemispherical device (82). A curved, arcuate, and/or dome-shaped support surface (86) extends from the base (84) to form the body of the device (82). Four orifices (88A, 88B, 88C, 88D) shown as grooves, recessions, and/or indentations are depicted formed in the front outer edge of the support surface (86), the orifice (88A, 88B, 88C, 88D) adapted for accommodating placement of a user's fingers, in the manner described above with regard to other embodiments. An additional orifice (90), depicted as a hole formed through the support surface (86) posterior to the first set of orifices (88A, 88B, 88C, 88D), is usable to accommodate a user's thumb. When a user's fingers and thumb are engage the support device (82) by inserted into and/or through the orifices (88A, 88B, 88C, 88D, 90), the palm of the user's hand can contact a weight-bearing portion (96) associated with and extending from the support surface (86). The depicted weight-bearing portion (96) is shown having a generally angled, dome shape with a curved front surface, having features aligned with the orifices (88A, 88B, 88C, 88D), e.g., for accommodating placement of a user's fingers, though other shapes and/or features can be used without departing from the scope of the present disclosure. In use, the user's fingers and thumb can remain suspended within the hollow interior of the device (82), while the user's wrist, fingers, and/or forearm can be aligned, as described above with reference to other embodiments. Further, during use, a user's heel can be suspended above the device (82) such that no significant weight is borne thereon, the majority of such weight being borne by the user's palm and/or knuckles.

A first set of engagement features (92A, 92B) is shown positioned at the sides of the device (82). FIG. 7A depict the engagement features (92A, 92B) as small holes formed through the support surface (86), usable to engage corresponding features (e.g., pins, protrusions, etc.) in a strap, band, or similar type of attachment; however, it should be understood that in other embodiments, the engagement features (92A, 92B) could include protruding members adapted for engagement with complementary recessions and/or orifices, or that other types of fasteners (e.g., snaps, clips, Velcro™, adhesives, etc.) could be used without departing from the scope of the present disclosure. A second set of engagement features (94A, 94B), also depicted as small holes formed through the support surface (86) is shown positioned below the first set of engagement features (92A, 92B), e.g., to allow engagement of the device (82) with an alternate type of band, strap, and/or similar attachment. The second set of engagement features (94A, 94B), while depicted as orifices, could include other types of fasteners and/or engagement members, as described above.

FIGS. 8A through 8F depict the support device (82) shown in FIGS. 7A through 7F, having a strap (98) associated therewith. The depicted strap (98) is shown engaged with the first set of engagement features (92A, 92B), e.g., through the alignment of holes within the strap (98) with the features (92A, 92B) to accommodate passage of a fastener (e.g., a pin, clip, etc.) therethrough; however, it should be understood that other means of engagement, such as protruding members extending from the strap (98) and/or the support surface (86) or fasteners (e.g., adhesives, Velcro™, snaps, magnets, etc.) could be used without departing from the scope of the present disclosure. The strap (98) is shown extending in front of the weight-bearing region (96) and above the orifices (88A, 88B, 88C, 88D), such that in use, the strap (98) would generally overlap and/or restrain a user's knuckles and/or the back of the user's hand, thereby limiting inadvertent upward and/or forward movement of the user relative to the device (82) and preventing unintended disengagement therefrom. While the strap (98) can include shape, dimensions, and/or material without departing from the scope of the present disclosure, in an embodiment, the strap (98) can be generally flexible and/or padded (e.g., formed from textiles, leather, rubber, plastic, etc.), and in a further embodiment, can be elastic in nature. In other embodiments, the strap (98) can be generally rigid and/or inelastic.

FIGS. 9A through 9F depict the support device (82) shown in FIGS. 7A through 7F, having a band (100) associated therewith. The band (100) is shown engaged with the second set of alignment feature (94A, 94B), e.g., through the alignment of holes (106A, 106B, shown in FIGS. 10A through 10E) with the alignment features (94A, 94B) to accommodate passage of a fastener (e.g., a pin, clip, etc.) therethrough; however, it should be understood that other means of engagement, such as protruding members extending from the band (100) and/or the support surface (86) or fasteners (e.g., adhesives, Velcro™, snaps, magnets, etc.) could be used without departing from the scope of the present disclosure. The band (100) is shown enclosing the front side of the support device (82) and overlapping the orifices (88A, 88B, 88C, 88D), such that in use, the band (100) can enclose a user's fingers and/or knuckles, thereby limiting inadvertent forward movement of the user relative to the device (82) and preventing unintended disengagement therefrom. While the band (100) can include shape, dimensions, and/or material without departing from the scope of the present disclosure, in an embodiment, the band (100) can be generally flexible and/or padded (e.g., formed from textiles, neoprene or other polymers, leather, rubber, plastic, etc.), and in a further embodiment, can be elastic in nature. In other embodiments, the band (100) can be generally rigid and/or inelastic.

Figure 10A:
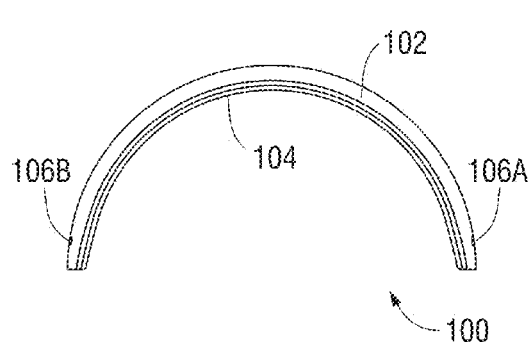
FIG. 10A depicts a top view of the band shown in FIG. 9A.
Figure 10B:
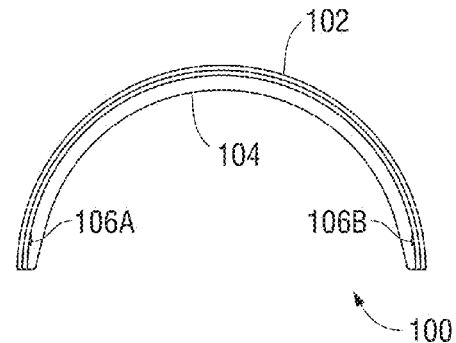
FIG. 10B depicts a bottom view of the band of FIG. 9A.
Figure 10D:
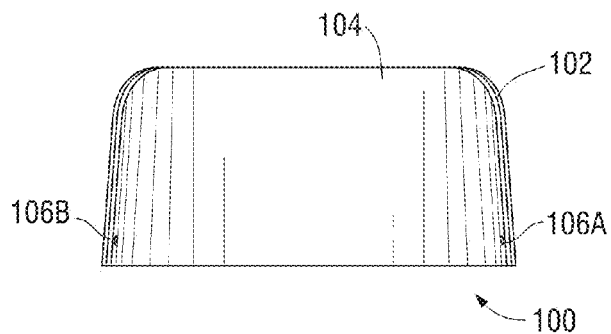
FIG. 10D depicts a back view of the band shown in FIG. 9A.
Figure 10C:
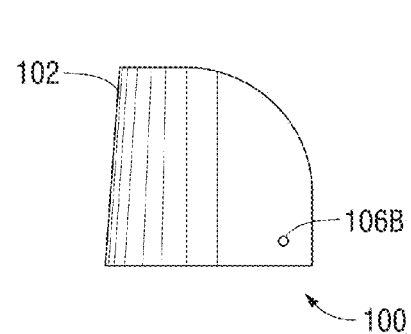
FIG. 10C depicts a Side view of the band of FIG. 9A.
Figure 10E:
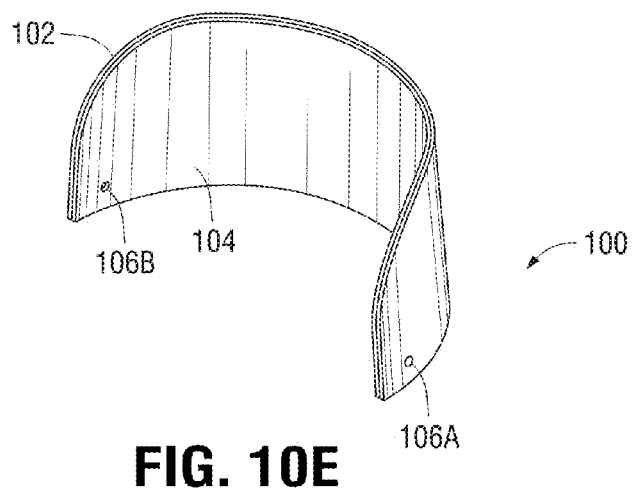
FIG. 10E depicts an isometric view of the band shown in FIG. 9A.

FIGS. 10A through 10E depict the band (100) removed from the support device. Specifically, FIG. 10A depicts a top view of the band (100), FIG. 10B depicts a bottom view, FIG. 10C depicts a side view, FIG. 10D depicts a back view, and FIG. 10E depicts an isometric view thereof. The band (100) is shown as a generally semi-circular, layered assembly having a front layer (102) positioned external to a rear layer (104). In an embodiment the front layer (102) can be formed from a generally rigid material to provide the band (100) with a fixed shape and to support the band (100) against a force applied by a user's hand, while the rear layer (104) can be formed from padded and/or compressible materials, e.g., to provide support to a users knuckles and/or fingers during use of the support device. It should be understood, however, that in various embodiments, the entirety of the band (100) could be rigid, compressible, flexible, elastic, and/or inelastic without departing from the scope of the present disclosure.

While the present disclosure describes a certain limited number of exemplary embodiments, it should be understood that the features of any individual embodiment herein could be combined with the features of any other embodiment without departing from the scope of the present disclosure of the invention; however, the specific features of one embodiment should not necessarily be attributed to other embodiments. Moreover, variations and modifications to the embodiments described herein may be evident to a person skilled in the art.

What is claimed:

1. A support device for protecting fingers, a wrist, a forearm, or combinations thereof by limiting movement thereof, the support device comprising:
    a base surface adapted to contact an object adjacent to the support device;
    a support surface extending from the base surface and comprising a curved shape, wherein the support surface is adapted to contact and support a hand of a user;
    a plurality of orifices formed in the support surface, wherein each of said orifices is adapted to receive a digit extending from the hand and suspend the digit between the support surface and the base surface while minimizing contact between the digit and the support surface and contact between the digit and the base surface;
    the base surface angled relative to the plurality of orifices for directing a load applied by the hand in a forward direction relative thereto such that a force applied to a heel of the hand is reduced and a force applied to a palm of the hand is increased;
    the base surface further angled such that a force is applied to metacarpophalangeal joints of the hand; and
    the support device further comprising padding positioned on the support surface, the padding adapted to contact the metacarpophalangeal joints.

2. The support device of claim 1, wherein the base surface is angled such that the heel of the hand is substantially suspended.

3. The support device of claim 1, wherein the support surface comprises an angled dome shape.

4. The support device of claim 1, wherein a first orifice of the plurality of orifices is positioned posterior relative to each other orifice of the plurality of orifices for retaining a thumb.

5. The support device of claim 4, wherein the support surface comprises a centerline defining a front side and a back side of the support surface, and wherein each other orifice of the plurality of orifices is formed in the front side.

6. The support device of claim 1, wherein the plurality of orifices comprise an angled orientation to further direct the load in the forward direction for reducing extension of the wrist.

7. The support device of claim 1, wherein the angle of the base is approximately 15 degrees.

8. The support device of claim 1, wherein the support surface is formed from substantially rigid material.

9. A support device for receiving and supporting a hand, the support device comprising:
    a generally flat base surface;

an arcuate support surface extending from the generally flat base surface, wherein the arcuate support surface comprises a front side and a back side;

a first orifice formed in the back side of the arcuate support surface;

at least one second orifice formed in the front side of the arcuate support surface, wherein the first orifice is adapted for receiving a thumb associated with the hand, wherein said at least one second orifice is adapted for receiving fingers associated with the hand, and wherein a portion of the arcuate support surface between the first orifice and said at least one second orifice is adapted to contact and support a palm associated with the hand; and the support device further comprising padding positioned in the portion of the support surface between the first orifice and said at least one second orifice, wherein the padding is adapted to contact metacarpophageal joints associated with the hand.

10. The support device of claim 9, wherein the generally flat base surface, the first orifice, said at least one second orifice, or combinations thereof is angled to direct a load applied by the hand toward the front side such that a force applied to a heel associated with the hand is reduced and a force applied to a palm associated with the hand is increased.

11. The support device of claim 10, wherein the generally flat base surface, the first orifice, said at least one second orifice, or combinations thereof, is angled approximately fifteen degrees.

12. The support device of claim 9, wherein the arcuate support surface comprises an angled dome shape.

13. The support device of claim 9, wherein the support surface is formed from substantially rigid material.

14. A method for supporting and limiting movement of a hand comprising a thumb, a plurality of fingers, a palm, a heel, metacarpophageal joints, and a wrist, the method comprising the steps of:

positioning a base of a support device against an adjacent object;

inserting the plurality of fingers in said at least one first orifice formed in a front side of the support device;

inserting the thumb in a second orifice formed in the support device posterior to said at least one first orifice; and contacting a support surface between said at least one first orifice and the second orifice with the palm and the metacarpophageal joints, thereby suspending the heel above the support device and aligning the wrist with the heel;

wherein the base is angled relative to at least one of said at least one first orifice and said second orifice for directing a load applied by the hand in a forward direction relative thereto such that a force applied to the heel of the hand is reduced and a force applied to the palm of the hand is increased, said base is further angled such that a force is applied to the metacarpophalangeal joints of the hand, the support device further comprising padding positioned on the support surface, the padding adapted to contact the metacarpophalangeal joints.

15. The method of claim 14, wherein the steps of inserting the plurality of fingers and inserting the thumb comprise suspending the thumb and the plurality of fingers while minimizing contact between the support device and the thumb and the plurality of fingers.

16. The method of claim 14, wherein the step of contacting the support surface comprises directing a force applied by the hand toward the front side of the support device.

* * * * *